US00PP20367P2

(12) United States Plant Patent
Perkins

(10) Patent No.: US PP20,367 P2
(45) Date of Patent: Sep. 29, 2009

(54) ***ANGELONIA* PLANT NAMED 'CAS WITE 09'**

(50) Latin Name: *Angelonia angustifolia*
Varietal Denomination: Cas Wite09

(75) Inventor: Ralph T. Perkins, Gilroy, CA (US)

(73) Assignee: Goldsmith Seeds, Inc., Gilroy, CA (US)

( * ) Notice: Subject to any disclaimer, the term of this patent is extended or adjusted under 35 U.S.C. 154(b) by 0 days.

(21) Appl. No.: 12/220,630

(22) Filed: Jul. 25, 2008

(51) Int. Cl.
*A01H 5/00* (2006.01)

(52) U.S. Cl. ..... Plt./404

(58) Field of Classification Search ..... Plt./263, Plt./404

See application file for complete search history.

*Primary Examiner*—Susan B McCormick Ewoldt
(74) *Attorney, Agent, or Firm*—S. Matthew Edwards

(57) ABSTRACT

A new *Angelonia* plant named 'Cas Wite09,' particularly distinguished by the clear white flower color, slightly upright and semi-trailing habit with dense foliage and branching, exceptional heat tolerance, and good vigor.

1 Drawing Sheet

Latin name of the genus and species of the plant claimed: *Angelonia angustifolia.*

Varietal denomination: 'Cas Wite09'.

BACKGROUND OF THE NEW PLANT

The present invention comprises a new *Angelonia,* botanically known as *Angelonia angustifolia,* and hereinafter referred to by the variety name 'Cas Wite09.'

'Cas Wite09' is a product of a planned breeding program. The new cultivar 'Cas Wite09' has a clear white flower color, slightly upright and semi-trailing habit with dense foliage and branching, exceptional heat tolerance, and good vigor.

'Cas Wite09' originated from a hybridization in a controlled breeding program in Gilroy, Calif. USA. The female parent was an unpatented hybrid seedling identified as '433-1' with lavender and white color. '433-1' has a lighter foliage color and is more upright in habit than 'Cas Wite09.'

The male parent of 'Cas Wite09' was an unpatented hybrid seedling identified as '407-3' with white color. '407-3' has a lighter foliage color, is more prostate in habit, and has smaller more cupped flowers than 'Cas Wite09.'

'Cas Wite09' was selected as one flowering plant within the progeny of the stated cross in 2006 in a controlled environment in Gilroy, Calif. USA.

The first act of asexual reproduction of 'Cas Wite09' was accomplished when vegetative cuttings were taken from the initial selection in June 2006. The pollination took place in September 2003 and the seed sowing in March 2006, all in a controlled environment in Gilroy, Calif. USA.

Horticultural examination of plants grown from cuttings of the plant initiated in June 2006 in Gilroy, Calif. USA, and continuing thereafter, has demonstrated that the combination of characteristics as herein disclosed for 'Cas Wite09' are firmly fixed and are retained through successive generations of asexual reproduction.

'Cas Wite09' has not been observed under all possible environmental conditions. The phenotype may vary significantly with variations in environment such as temperature, light intensity and day length.

A Plant Breeder's Right for this cultivar was applied for in Canada on Dec. 24, 2007. 'Cas Wite09' has not been made publicly available more than one year prior to the filing of this application.

DESCRIPTION OF THE DRAWING

The accompanying photographic drawing shows typical flower and foliage characteristics of 'Cas Wite09' with colors being as true as possible with an illustration of this type. The photographic drawing shows a flowering potted plant of the new variety and a close-up of the flowers. Both photographs were taken in the spring of 2008 in Gilroy, Calif. USA. Both were grown in Gilroy, Calif. USA and were approximately 3–4 months old.

DETAILED BOTANICAL DESCRIPTION

The measurements were taken in Gilroy, Calif. USA, in April 2008 on plants that were growing in gallon pots. Culture of these plants started in about January in a greenhouse. The plant was about 3 months old.

Color Chart used: Royal Horticultural Society Colour Chart (R.H.S.) 2001

BRIEF SUMMARY OF INVENTION

The following observations, measurements, and comparisons describe plants grown in a greenhouse in Gilroy, Calif. USA. The following traits have been repeatedly observed and are determined to be basic characteristics of the new variety. The combination of these characteristics distinguishes this *Angelonia* as a new and distinct variety.

TABLE 1

DIFFERENCES BETWEEN THE NEW VARIETY 'CAS WITE09' AND SIMILAR VARIETY

| | 'Cas Wite09' | 'Balangbawi' (U.S. Plant Pat. No. 16,555) |
|---|---|---|
| Flower size/shape | Larger/flatter | Smaller/more cupped |
| Branching habit | Better/more branching | Less branching |
| Foliage color | Darker | Lighter |

Plant:

*Form, growth and habit.*—Upright and semi-trailing, good vigor and branching.

*Plant height.*—10–13 cm.
*Plant height (inflorescence included).*—12–16 cm.
*Plant width.*—35–40 cm.

Foliage:
*Immature, leaf color, upper surface.*—Closest to RHS 143A.
*Lower surface.*—RHS 137B.
*Mature, leaf color, upper surface.*—RHS 137A.
*Lower surface.*—RHS 137B.
*Length.*—8.3–9.2 cm.
*Width.*—0.7–0.8 cm.
*Shape.*—Narrowly elliptical.
*Base shape.*—Cuncate.
*Apex shape.*—Acute.
*Margin.*—Serrate.
*Texture.*—Glandular hairs on both surfaces.
*Color of veins, upper surface.*—RHS 144B.
*Color of veins, lower surface.*—RHS 144B.

Stem:
*Number of main stems per plant.*—About 10.
*Number of leaves per stem (before it branches).*—14–18 excluding peduncle.
*Color of stem.*—RHS 144B.
*Length of stem.*—25–30 cm.
*Diameter.*—0.3–0.4 cm.
*Length of internodes.*—2.0–3.0 cm.
*Texture.*—Glandular hairs.

Inflorescence:
*Type.*—Terminal raceme; florets solitary in leaf axis.
*Number of florets per raceme.*—12–18 flowers, + 4–8 buds.
*Raceme length.*—9.5–13.0 cm.
*Color of pedicel.*—RHS 144C.
*Length of pedicel.*—1.0–1.4 cm.
*Diameter of pedicel.*—0.075 cm.
*Texture.*—Glandular hairs.

Corolla:
*Form.*—Single, two-lipped (5-petaled, fused at base).
*Length of floret.*—2.7–2.9 cm.
*Width of floret.*—2.6–2.8 cm.
*Color upper lip petals, upper surface.*—RHS N155B but whiter.
*Color upper lip petals, lower surface.*—RHS N155B but whiter.
*Size upper lip petal length.*—0.8–0.9 cm from corolla opening.
*Size upper lip petal width.*—1.0–1.1 cm.
*Color lower lip, lateral petals, upper surface.*—RHS N155B but whiter.
*Color lower lip, lateral petals, lower surface.*—RHS N155B but whiter.
*Size lower lip, lateral petals length.*—0.7–0.9 cm from corolla opening.
*Size lower lip, lateral petals width.*—1.0–1.1 cm.
*Color lower lip, mid-petal, upper surface.*—RHS N155B but whiter.
*Color lower lip, mid-petal, lower surface.*—RHS N155B but whiter.
*Size lower lip, mid-petal length.*—1.0–1.1 cm from corolla opening.
*Size lower lip, mid-petal width.*—0.8–1.0 cm.
*Petal shape.*—Obovate.
*Apex shape.*—Rounded to obtuse.
*Margin.*—Entire.
*Petal texture.*—Papillose; few glandular hairs on both surfaces.
*Corolla color, inside.*—RHS N155B but whiter with RHS 144A spots basally at the transition point to the lower lip.
*Corolla color, outside.*—RHS N155B but whiter with RHS 144A spots basally at fusion point to lower lip.
*Duration of flowering.*—Continuous flowering throughout the summer.
*Fragrance.*—Slight to none.
*Lastingness of individual florets.*—About 7 days.

Bud (just before opening):
*Color.*—RHS 154D.
*Length.*—0.7–0.9 cm.
*Width.*—0.5–0.8 cm.
*Shape.*—Orbicular.

Calyx:
*Number of sepals.*—5, fused at base.
*Color of sepals.*—RHS 146B.
*Length of sepals.*—0.3–0.4 cm.
*Width of sepals.*—0.2 cm.
*Sepal shape.*—Ovate.
*Apex shape.*—Acute.
*Margins.*—Entire.
*Texture.*—Glandular hairs on outer surface, smooth on the inner surface.

Reproductive organs:
*Pistil.*—1.
*Length.*—0.5 cm.
*Style color.*—RHS N155B but whiter.
*Stigma color.*—RHS N155N but whiter.
*Number of stamens.*—4 in pairs.
*Length filaments.*—0.3 cm.
*Color of filaments.*—RHS N155B but whiter.
*Pollen amount.*—Scarce.
*Color of pollen.*—RHS 155.
*Fertility/seed set.*—Not observed on this hybrid.

Disease/pest resistance: Disease resistance and/or susceptibility has not been observed on this hybrid.

What is claimed is:

1. A new and distinct variety of *Angelonia* plant named 'Cas Wite09,' substantially as illustrated and described herein.

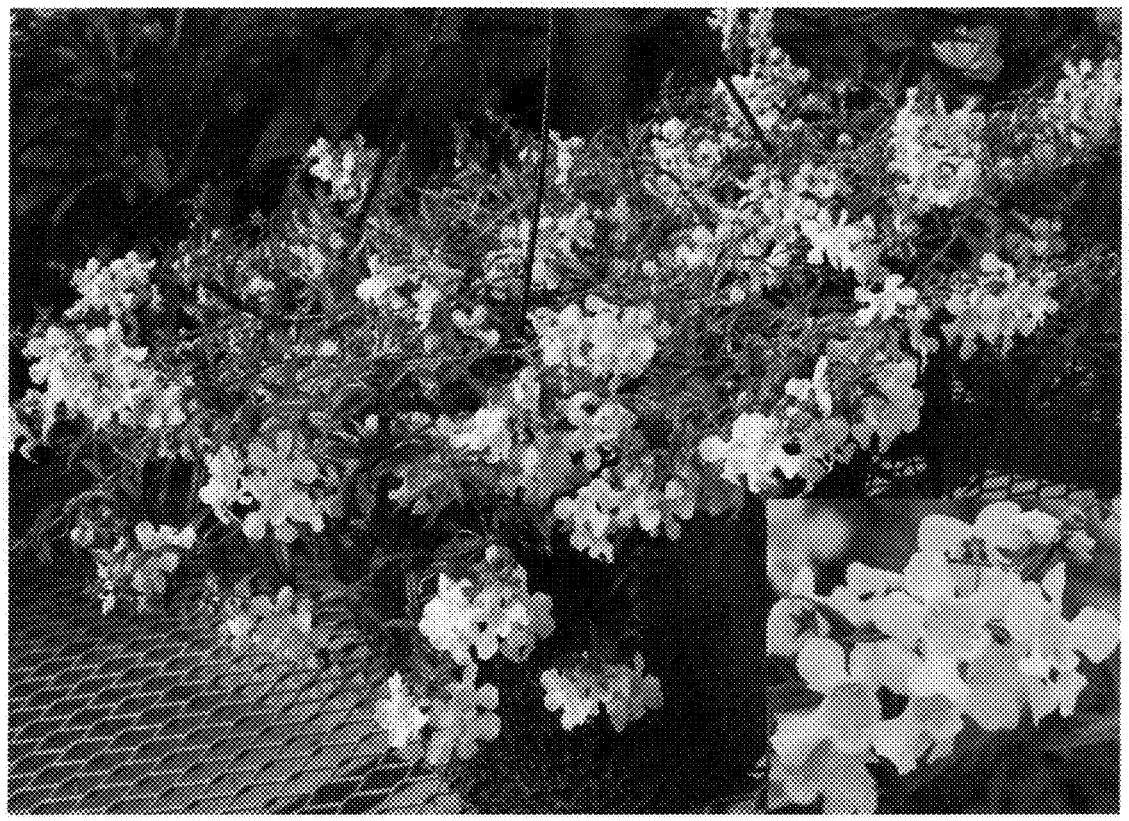

* * * * *